United States Patent
Christopher et al.

(10) Patent No.: US 10,105,086 B2
(45) Date of Patent: Oct. 23, 2018

(54) TWIST-TO-CHARGE MECHANISM OF LANCING DEVICE

(71) Applicant: FACET TECHNOLOGIES, LLC, Kennesaw, GA (US)

(72) Inventors: James M. Christopher, Dacula, GA (US); Lauren R. Pusey, Woodstock, GA (US); Jeremy Rodgers, Marietta, GA (US)

(73) Assignee: FACET TECHNOLOGIES, LLC, Kennesaw, GA (US)

( * ) Notice: Subject to any disclaimer, the term of this patent is extended or adjusted under 35 U.S.C. 154(b) by 1255 days.

(21) Appl. No.: 13/975,892

(22) Filed: Aug. 26, 2013

(65) Prior Publication Data
US 2014/0058428 A1  Feb. 27, 2014

Related U.S. Application Data

(60) Provisional application No. 61/693,467, filed on Aug. 27, 2012.

(51) Int. Cl.
*A61B 5/151* (2006.01)
*A61B 5/15* (2006.01)

(52) U.S. Cl.
CPC ...... *A61B 5/15117* (2013.01); *A61B 5/15019* (2013.01); *A61B 5/1519* (2013.01);
(Continued)

(58) Field of Classification Search
CPC ............ A61B 5/15019; A61B 5/15029; A61B 5/150297; A61B 5/150412; A61B 5/1519;
(Continued)

(56) References Cited

U.S. PATENT DOCUMENTS 5,318,584 A   6/1994  Lange et al.
5,984,940 A   11/1999  Davis et al.
(Continued)

FOREIGN PATENT DOCUMENTS

EP         2263543 A1    12/2010
WO    WO2012081807    *  9/2011  ......... A61B 5/15126

OTHER PUBLICATIONS

International Search Report and Written Opinion of PCT/US2013/056623; dated Dec. 11, 2013; 14 pgs.

*Primary Examiner* — Christopher L Templeton
*Assistant Examiner* — Majid Jamialahmadi
(74) *Attorney, Agent, or Firm* — Gardner Groff Greenwald & Villanueva, PC

(57) ABSTRACT

A lancing device includes a housing, a lancet carrier translational within the housing, a drive spring for propelling the lancet carrier through a translational lancing stroke, and a charging mechanism. The charging mechanism includes a first cam member that is rotatable relative to the housing, a second cam member that abuts the first cam member, is coupled to the lancet carrier, and is restricted from rotation relative to the housing, and a rotatable handle co-rotationally attached to the first cam member. Rotation of the handle rotates the first cam member with it, causing the first cam member to rotate against the second cam member, which in response traverses axially because it is restricted from rotation, thereby retracting the lancet carrier to a retracted or charged state.

20 Claims, 13 Drawing Sheets

(52) U.S. Cl.
CPC .... *A61B 5/150022* (2013.01); *A61B 5/15029* (2013.01); *A61B 5/15113* (2013.01); *A61B 5/15128* (2013.01); *A61B 5/15194* (2013.01); *A61B 5/150297* (2013.01); *A61B 5/150412* (2013.01); *A61B 5/150503* (2013.01); *Y10T 29/49826* (2015.01)

(58) Field of Classification Search
CPC ............ A61B 5/15128; A61B 5/15113; A61B 5/15117; A61B 5/15194; A61B 5/1411; A61B 5/15142; A61B 5/15186; A61B 5/15146; A61B 5/15192
USPC ................................................. 606/181, 182
See application file for complete search history.

(56) References Cited

U.S. PATENT DOCUMENTS

| | | | |
|---|---|---|---|
| 6,056,765 A | | 5/2000 | Bajaj et al. |
| 6,156,050 A | * | 12/2000 | Davis ................. A61B 5/15186 |
| | | | 606/181 |
| 6,419,661 B1 | | 7/2002 | Kuhr et al. |
| 6,558,402 B1 | * | 5/2003 | Chelak ................. A61B 5/1411 |
| | | | 600/583 |
| 7,105,006 B2 | | 9/2006 | Shraga |
| 7,621,931 B2 | | 11/2009 | Shraga |
| 7,670,352 B1 | * | 3/2010 | Starnes ............ A61B 5/150183 |
| | | | 600/583 |
| 8,002,785 B2 | | 8/2011 | Weiss et al. |
| 8,317,812 B2 | | 11/2012 | Lum |
| 2005/0143767 A1 | * | 6/2005 | Kimura .............. A61B 17/1222 |
| | | | 606/158 |
| 2013/0274781 A1 | * | 10/2013 | Cha .................... A61B 5/15113 |
| | | | 606/182 |

\* cited by examiner

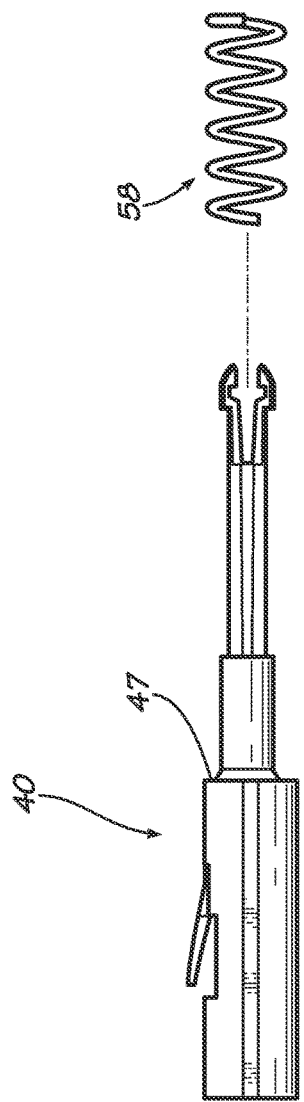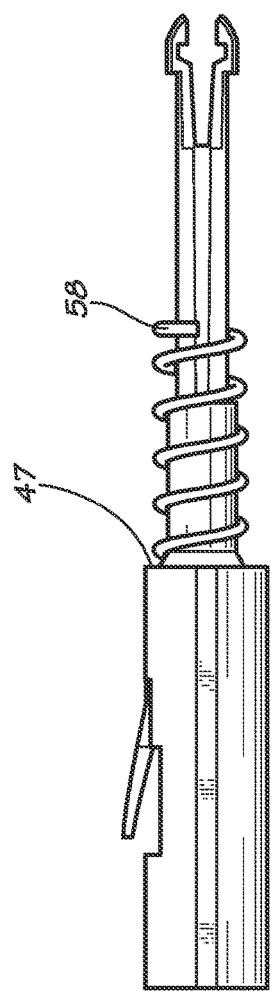
FIG. 9A
FIG. 9B

TWIST-TO-CHARGE MECHANISM OF LANCING DEVICE

CROSS-REFERENCE TO RELATED APPLICATION

This application claims the priority benefit of U.S. Provisional Patent Application Ser. No. 61/693,467 filed Aug. 27, 2012, the entirety of which is hereby incorporated herein by reference for all purposes.

TECHNICAL FIELD

The present invention relates generally to the field of medical devices, and more particularly to a lancing device for blood sampling and testing with a mechanism for charging the lancet drive mechanism by a twisting motion.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other biasing means of the drive mechanism, and a release mechanism for releasing the drive mechanism upon actuation. A lancet is typically propelled by the drive mechanism from a retracted position within the housing to an extended position wherein a sharp tip portion of the lancet projects from the housing to prick the subject's skin at a lancing site. Optionally, a depth-adjust mechanism may be included for providing adjustment to the depth of penetration of the sharp tip portion projecting external of the housing.

Many known lancing devices use charging mechanisms that function to charge the drive mechanism by pulling or pushing an actuator handle of the mechanism generally away from the body of the lancing device. This can present challenges to users with reduced manual dexterity, and may require using two hands to hold the device body and pull the handle until the device is charged. Moreover, these pushing or pulling charging motions involve a frictional component that must be overcome to charge the device, commonly resulting in the subject or user having to exert additional force.

Additionally, the assembly of lancing devices commonly includes a multi-step process that can include pre-assembly, welding, and snapping or gluing together portions of the device or the housings, and often requires costly equipment such as a pneumatic press to carry out the snapping procedure. These required assembly steps, procedures, and equipment are often seen as drawbacks to making lancing devices, as they tend to increase the cost of the lancing devices.

Continuing improvement to charging features and the assembly of lancing devices is sought. It is to the provision of improved lancing devices and methods of operation, use, and assembly thereof that the present invention is primarily directed.

SUMMARY

In example embodiments, the present invention provides a lancing device having improved charging features, and optionally includes an integrated depth-adjustment mechanism. Additional example embodiments of the present invention provide improved methods of operation, use, and assembly of lancing devices.

In one aspect, the present invention relates to a lancing device that includes a housing, a lancet carrier translational within the housing, a drive spring for propelling the lancet carrier through a translational lancing stroke, and a charging mechanism. The charging mechanism includes a first cam member that is rotatable relative to the housing, a second cam member that abuts the first cam member, is coupled to the lancet carrier, and is restricted from rotation relative to the housing, and a rotatable handle co-rotationally attached to the first cam member. Rotation of the handle rotates the first cam member with it, causing the first cam member to rotate against the second cam member, which in response traverses axially because it is restricted from rotation, thereby retracting the lancet carrier to a retracted or charged state. A release mechanism is then actuated to release the lancet carrier to traverse the lancing stroke.

In another aspect, the invention relates to a charging mechanism for a lancing device having a housing and a lancet carrier translational therein in an axial direction. The charging mechanism includes a first cam member axially stationary relative to the housing and rotational relative to the housing, a second cam member that abuts the first cam member, axially retracts to retract the lancet carrier, and is restricted from rotation relative to the housing, and a rotatable handle co-rotationally attached to the first cam member. Rotation of the handle rotates the first cam member with it, causing the first cam member to rotate against the second cam member, which in response traverses axially because it is restricted from rotation, thereby retracting the lancet carrier to a retracted or charged state. A release mechanism of the lancing device is then actuated to release the lancet carrier to traverse the lancing stroke.

In still another aspect, the invention relates to methods of assembling a lancing device. In example forms, the assembly method includes retaining a drive spring on a portion of the lancet carrier, forming a subassembly by connecting a charging mechanism to the lancet carrier (with the drive spring still retained thereon), positioning the subassembly axially within a housing having an axial internal bore, and coupling a retaining member into aligned channels formed along at least a portion of the periphery of the housing and the charging mechanism. All of these assembly steps can be performed linearly along the longitudinal axis of the housing, without the time and cost of assembling conventional lancing devices.

In yet another aspect, the present invention relates to methods of operating a lancing device. In example forms, the operation method includes providing the lancing device with a housing with an axial internal bore, a lancet carrier translational therein, a drive spring for propelling the lancet carrier through a translational lancing stroke, and a charging mechanism. The charging mechanism may include a first cam member axially stationary relative to the housing and rotational relative to the housing, a second cam member that abuts the first cam member, axially retracts to retract the lancet carrier, and is restricted from rotation relative to the housing, and a rotatable handle co-rotationally attached to the first cam member. The operational method further comprises rotating the handle, which rotates the first cam member with it, which causes the first cam member to rotate against the second cam member, which in response traverses axially because it is restricted from rotation, which retracts the lancet carrier to a retracted or charged state. The operational method further comprises actuating a release member to release the lancet carrier to traverse the lancing stroke.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of example embodiments of the invention, and are not restrictive of the invention, as claimed.

BRIEF DESCRIPTION OF THE DRAWINGS

FIGS. 9a and 9b are side views of a portion of the lancing device of FIG. 8, showing a step of the assembly process.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In example embodiments, the present invention relates to an innovative charging mechanism for a lancing device, a lancing device with such a charging mechanism, and methods of operation, use, and assembly of lancing devices for example with such a charging mechanism. In example forms, the lancing device includes a housing having a lancet opening through which a sharp tip of a lancet extends in an extended position of a lancing stroke, a lancet carrier carrying the lancet and translationally moveable within the housing through the lancing stroke, a drive spring that propels the lancet carrier through the lancing stroke, and a charging mechanism. The charging mechanism includes a first cam member that is rotatable relative to and about the axis of the lancet carrier and the housing, a second cam member that abuts the first cam member, is coupled to the lancet carrier, and is restricted from rotation relative to the housing, and a rotatable handle co-rotationally attached to the first cam member. Rotation of the handle co-rotates the first cam member with it, causing the first cam member to rotate against the second cam member, which in response traverses axially because it is restricted from rotation, thereby retracting the lancet carrier to a retracted or charged state. Optionally, a depth-adjustment mechanism can be provided for selectively controlling the depth of penetration of a lancet when projecting external of the housing (including endcap) of the lancing device 10.

Figure 1:
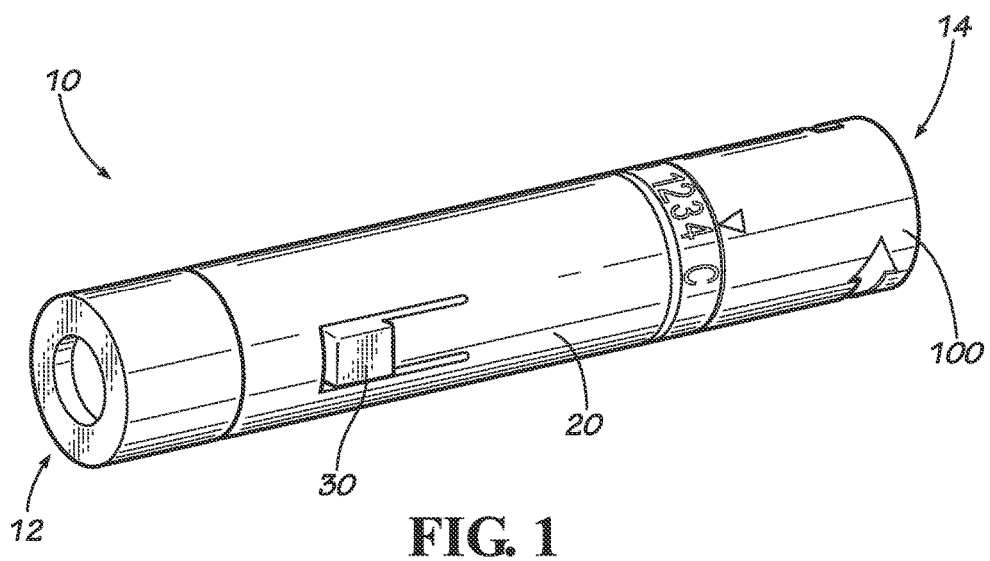
FIG. 1 is a front perspective view of a lancing device according to an example embodiment of the present invention.
Figure 2:
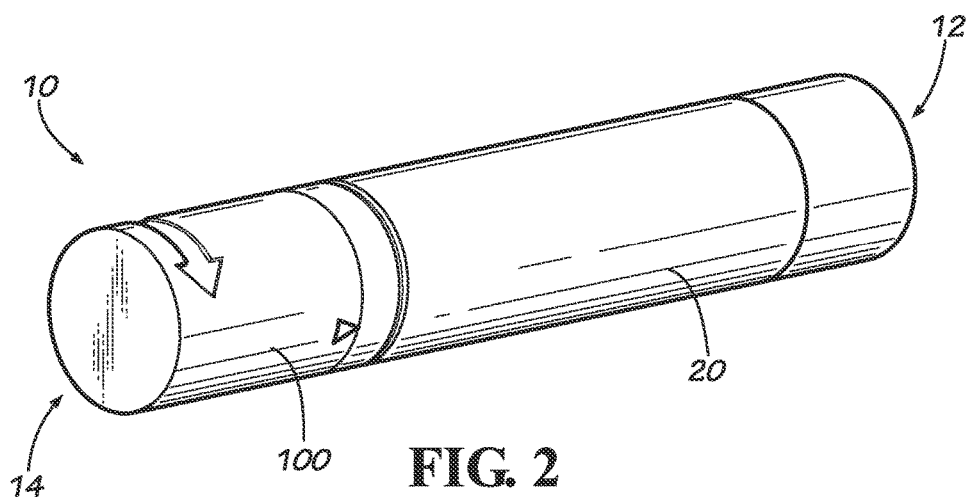
FIG. 2 is a rear perspective view of the lancing device of FIG. 1.
Figure 3:
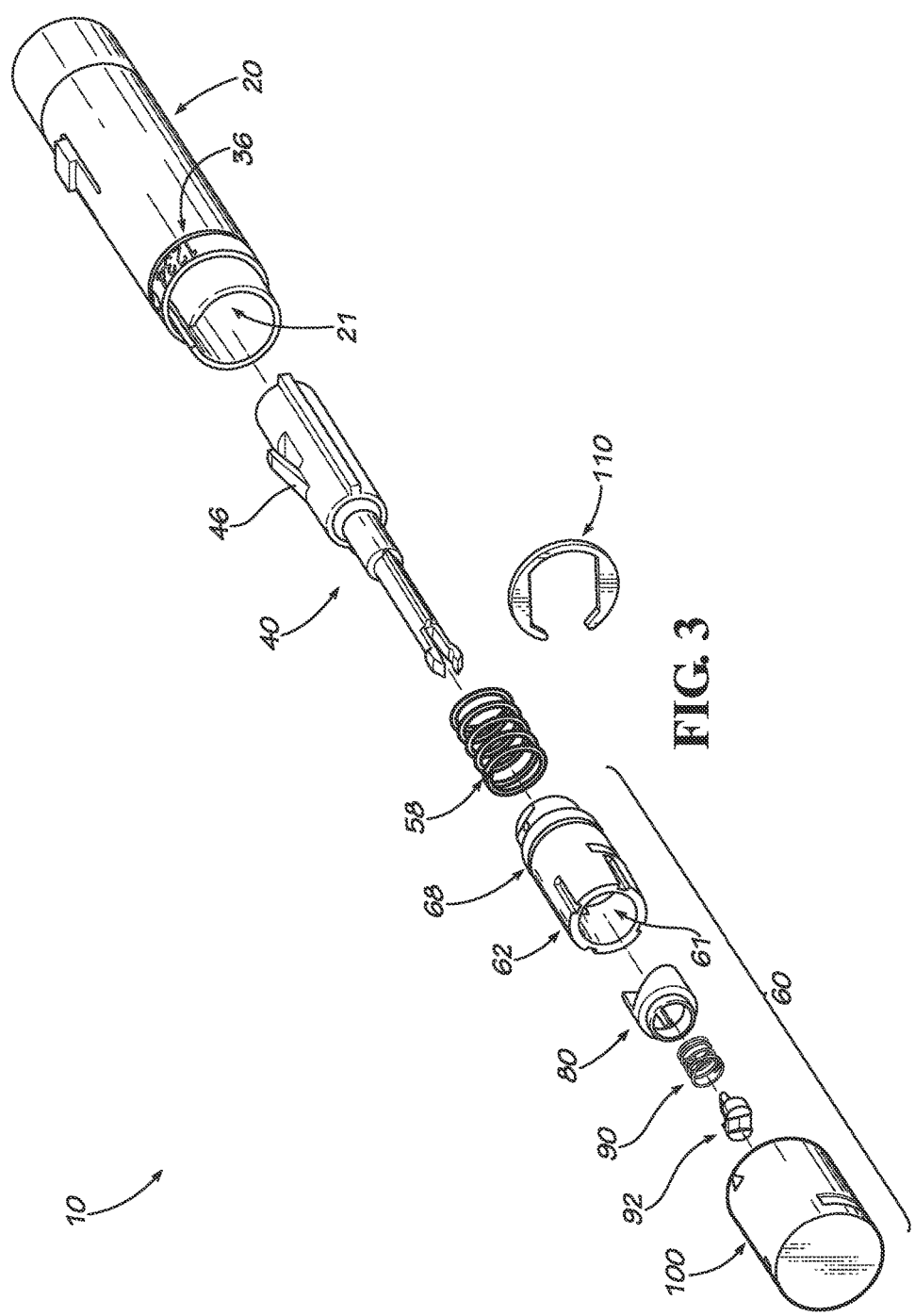
FIG. 3 is a rear exploded perspective view of the lancing device of FIG. 1.

With reference now to the drawing figures, wherein like reference numbers represent corresponding parts throughout the several views, FIGS. 1-14C show a lancing device 10 according to an example form of the present invention. With particular reference to FIGS. 1-3, the lancing device 10 is preferably compact, and in the depicted embodiment has a generally cylindrical, narrow-profile, elongate outer geometry, for example having an aspect ratio (length:diameter) of at least 3:1.

The lancing device 10 generally comprises an outer housing 20, a lancet carrier 40 (e.g., a drive plunger), and a charging mechanism 60. The housing has a bore 21 extending axially therethrough that holds the lancet carrier 40 and portions of the charging mechanism 60. Optionally, a depth adjustment mechanism can be incorporated therein for adjusting the depth of penetration of the lancet (as described below). A drive spring 58 is operably engaged between the lancet carrier 40 and a portion of the charging mechanism 60, and a return spring 90 is operably engaged between a portion of the charging mechanism 60 and a tail portion 47 of the lancet carrier 40. Optionally, the end retainer attachment 92 couples to the tail portion 47 to retain the return spring 90 thereon. In alternate embodiments, a single spring element functions to drive and return the lancet. In example forms, the charging mechanism 60 comprises two cam members (described below) for charging the lancing device 10 (i.e., retracting the lancet carrier 40 to energize the drive spring 58) by twisting or rotating a handle 100 rotationally mounted to the distal end 14 of the housing 20.

Figure 4:
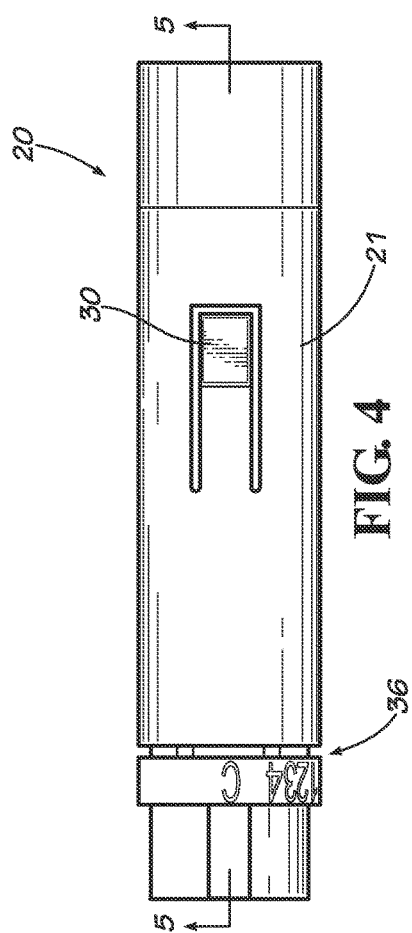
FIG. 4 is a top view of a housing of the lancing device of FIG. 1.
Figure 5:
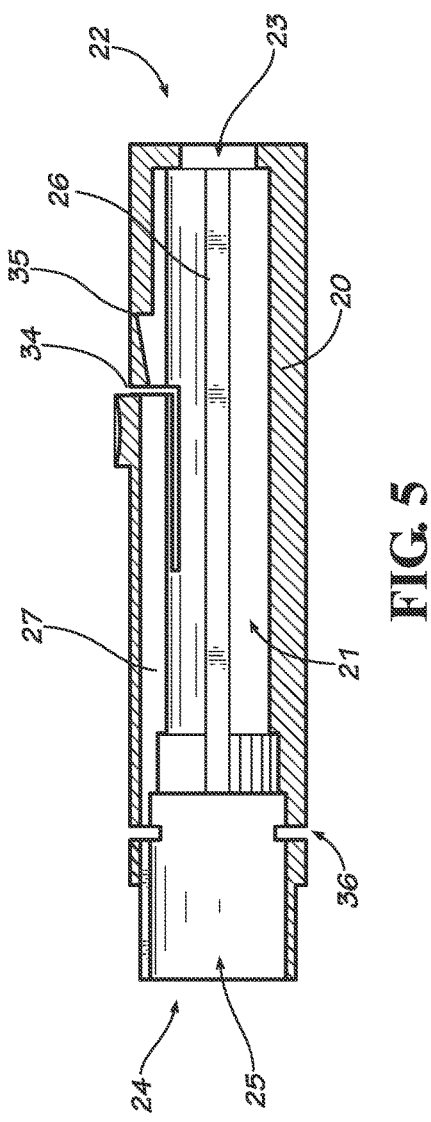
FIG. 5 is a cross-sectional view of the housing of FIG. 4 taken a line 5-5.

FIGS. 4-5 show the housing 20 generally comprising a cylindrical sleeve having a proximal cylindrical section 22 defining a lancet opening 23, and a distal cylindrical section 24 defining an opening 25 to provide for assembly therein. The housing 20 is generally hollow, with the internal bore 21 extending axially from the proximal section 22 to the distal section 24. In alternative embodiments, the housing has a transverse cross-section that is rectangular, polygonal, or another regular or irregular shape.

The housing 20 may include one or more guidance elements 26 that engage guidance elements 44 of the lancet carrier 40 to provide translational guidance to the lancet carrier and restrict relative rotational movement. In the depicted embodiment, for example, the housing guidance elements 26 are provided by one or more guidance channels formed longitudinally in/along the inner wall of the housing 20, and the lancet-carrier guidance elements 44 are provided by one or more wings projecting laterally (e.g., radially) outward from the lancet carrier 40 and slidingly received in the guidance channels. The housing guidance channels 26 can be in the form of any slotted or recessed surface and thus can have a profile that is rectangular, semi-circular, or another regular or irregular shape, so long as they slidingly receive the lancet-carrier wings 44 to translationally guide the lancet carrier 40 and restrict it from rotation relative to the housing 20. And the lancet-carrier guidance wings 44 can be in the form of any projecting member and thus can have a profile that is rectangular, semi-circular, or another regular or irregular shape, so long as they are slidingly received in the housing guidance channels 26 to translationally guide the lancet carrier 40 and restrict it from rotation relative to the housing 20.

In other embodiments, the arrangement is vice versa, with the guidance channels formed longitudinally along the lancet carrier and the lateral wings extending inward from the housing inner wall. Typically, there are two guidance channels 26 and two guidance wings 44, with the channel-and-wing pairs positioned on opposite sides of the housing 20 (about 180 degrees apart), though in other embodiments more or fewer are provided in the same or other positions to provide the same functionality.

A release mechanism is provided for releasably retaining the lancet carrier 40 in the charged position and then releasing or triggering it to be propelled under the influence of the drive spring 58. Typically, the release mechanism includes a catch surface on the lancet carrier 40 that is releasably engaged by a retainer surface on or connected to a release actuator. In the depicted embodiment, for example, the release mechanism includes a release button actuator 30 on a portion of the housing 20 for removing a release finger 46 of the lancet carrier 40 (see FIG. 6) from a trigger catch face 34 of the housing 20. Such removal/release initiates the lancing stroke and results in the lancet carrier 40 moving under the influence of the drive spring 58 from a retracted position within the housing 20 to an advanced/extended position wherein at least the sharp lancet tip (unshown) projects externally from the housing through the lancing opening 23 to penetrate the subject's skin at a lancing site.

The release button 30 is preferably formed as an integral part of the housing 20 and has a substantially low profile with a raised portion proximal the free end of the release button 30 minimally projecting beyond the outer surface of the housing 20. In example forms, a trigger slot 27 is formed along the inner portion of the housing 20 and axially aligns with the lengthwise axis of the release button 30, thereby providing a path to accommodate the assembly and function of the lancet carrier 40 and the release finger 46 mounted thereto. Optionally, the release button can be separable and/or comprise any desired profile. In other embodiments, the release mechanism includes another type of conventional or new catch/release mechanism for releasably retaining the lancet carrier in the charged position and then releasing or triggering it to be propelled under the influence of the drive spring.

To accommodate coupling portions of the charging mechanism 60 within the housing 20, a substantially circumferential channel 36 can be provided near the distal end 24 of the housing 20 along the outer periphery thereof. The channel 36 may include at least one opening extending within the internal bore 21 (as will be described below). Optionally, a plurality of depth-indication markings can be provided along the periphery of the housing 20 to correspond with a plurality of depth settings (as will be described below).

Figure 6:
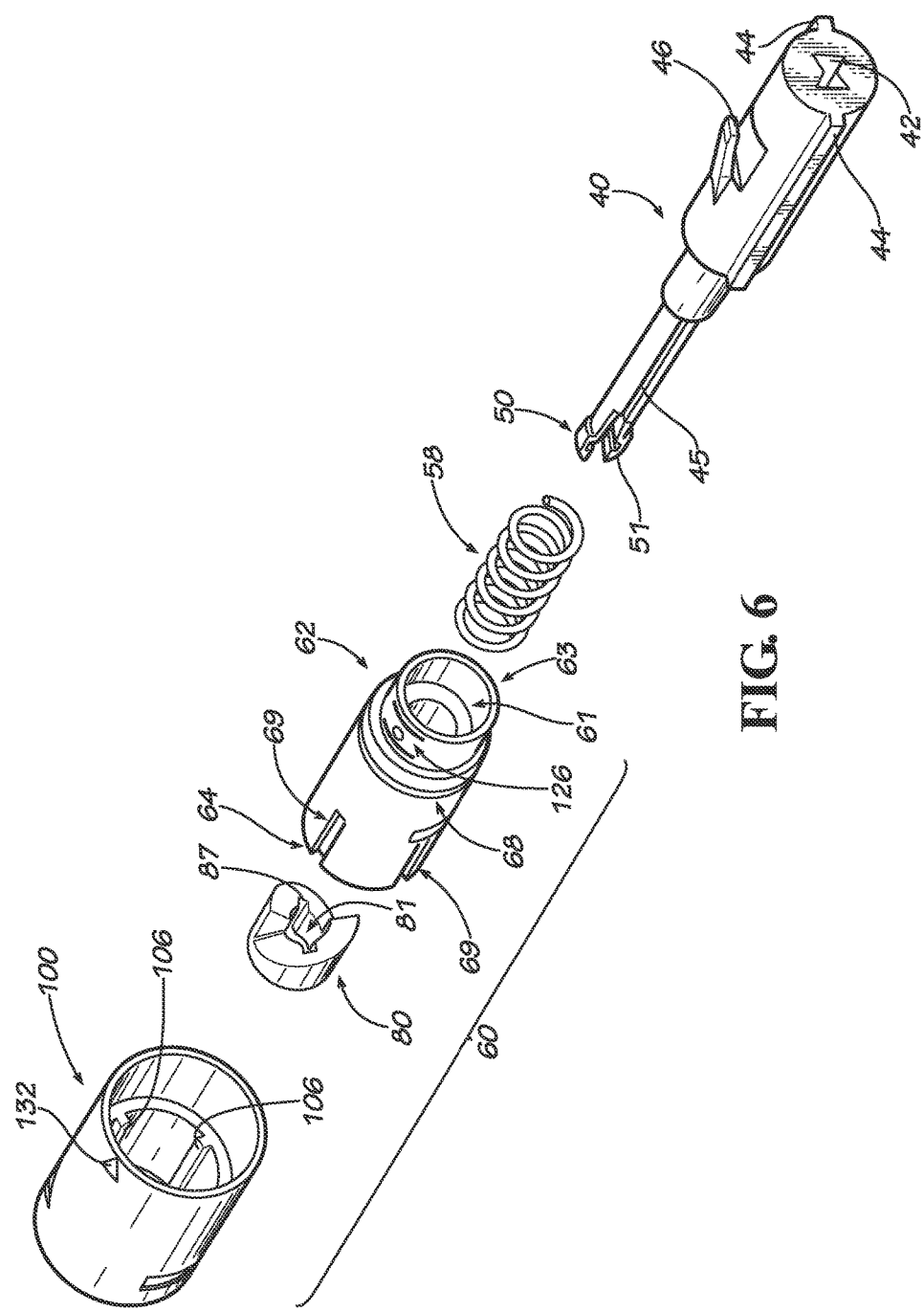
FIG. 6 is a front exploded view of a portion of the lancing device of FIG. 3 with portions removed to show internal components thereof.

As shown in FIGS. 3 and 6, the lancet carrier 40 is generally elongate and extends from a proximal end (defining a proximal portion) to a distal end (defining a distal portion) for translational movement within the axially extending bore 21 of the housing 20. The proximal end portion of the lancet carrier 40 includes a lancet receiver 42 for releasably engaging a lancet (unshown) of standard or customized configuration. The receiver 42 can be in the form of for example a six-sided orifice as depicted, or a collar or sleeve of the same or another shape, that retains the lancet with a friction fit.

The proximal end portion of the lancet carrier 40 includes one or more of the laterally projecting guide wings 44 that extend outward from the outer face of the lancet carrier 40 and slide within the guide slots 26 of the housing 20. Engagement of the guide wings 44 within the guide slots 26 serves to prevent rotation of the lancet carrier 40, while still permitting translation, relative to the housing 20. In other embodiments, the wings and the slots are reversed, with the wings extending inward from the inner wall of the housing 20 and the slots formed on the carrier 40, as noted above. And in other embodiments, other conventional cooperating guidance elements can be provided on the housing and the lancet carrier for preventing relative rotation but permitting relative translation of these parts.

A flexible trigger arm 46 of the charging mechanism 60 extends in a cantilevered fashion outwardly from the proximal portion of the lancet carrier 40, and is received in the trigger slot 27 of the housing 20. The trigger slot 27 extends from the distal end 24 of the housing to an inner surface defined by the lancet opening 23 at the proximal end 22. In example forms, the free end of the trigger arm 46 releasably engages against the contact face 34 of the housing 20 to retain the lancet carrier 40 in its charged state until being disengaged from the contact face by actuation of the release button 30. Optionally, a stop surface 35 is provided within the trigger slot 27 between the contact face 34 and the lancet opening 23 for generally defining the maximum depth of penetration of the lancet carrier 40 traversing therein. And in other embodiments, the lancet carrier includes another conventional or new feature for being releasably retained and then launched through the lancing stroke by operation of the release mechanism.

The distal portion of the lancet carrier 40 may be shaped and sized to retain thereon the drive spring 58, as well as other components of the charging mechanism 60 (as described below). For example, the distal portion of the lancet carrier 40 may include a resiliently flexing tail portion (e.g., two spaced-apart cantilevered arms that resiliently deflect inward towards each other to provide clearance) 50 with a retainer projection (e.g., an outwardly extending flange, ridge, collar, or tab) 51 formed at the distal end, as depicted. The drive spring 58 (and another component of the charging mechanism 60) are coaxially held on the tail portion 50 and retained there by the lancet-carrier retainer projection 51. The two arms of the resiliently flexing tail portion 50 define a slot between them along the length of the arms to permit the opposed arms to be flexed inwardly toward or outwardly away from one another to receive portions of the charging mechanism 60 and the return spring 90, and to also receive and provide engagement with the end retainer attachment 92.

In addition, the distal portion of the lancet carrier 40 may include one or more keyed elements 45 that engage mating keyed elements of the charging mechanism 60 (as described below). In other embodiments, the lancet carrier has another conventional or new design for providing operational engagement by the drive and return springs and other elements of the charging mechanism.

FIG. 6 shows a partial assembly view of the lancing device 10, with portions removed to better show details of the charging mechanism 60. The charging mechanism 60 includes a first cam member 62, a second cam member 80, and a charging handle 100. Rotating (twisting) the handle 100 causes the first cam member 62 to rotate, which axially displaces the second cam member 80, which axially retracts the lancet carrier 40 to charge the drive spring 58.

The first cam member 62 may be generally elongate, extend from a proximal end 63 to a distal end 64, and be sized and shaped to fully or partially mount within the housing 20 and cooperate with portions therein. In addition, the first cam member 62 may have an axial bore 61 extending therethrough that is sized and shaped so that its proximal end 63 fully or partially receives the drive spring 58 and the lancet carrier 40, while allowing the lancet carrier to traverse therethrough. Furthermore, the axial bore 61 of the first cam member 62 may be sized and shaped so that its distal end 64 fully or partially receives the second cam member 80, while allowing the second cam member to traverse therethrough. In other embodiments, the first cam member does not receive any portion of the lancet carrier, and instead the second cam member extends at least partially from its proximal end 63 to engage the lancet carrier external to the first cam member, or the lancet carrier tail portion includes an axial bore sized to receive the first cam member therein.

In addition, the first cam member 62 and the handle 100 include mating co-rotation elements so that the first cam member rotates in response to rotation of the handle. In the depicted embodiment, for example, the first cam member 62 includes mounting slots 69 to accommodate engagement with inwardly projecting mounting ribs 106 of the changing handle 100. In other embodiments, the arrangement is vice versa, with mounting slots of the changing handle receiving outwardly projecting mounting ribs of the first cam member. In other embodiments, the first cam member and the handle include other conventional structures operably coupling them together to provide co-rotation. And in other embodiments, the first cam member and the handle are integrally formed as a single part.

The mounting slots 69 of the first cam member 62 have ends beyond which the mounting ribs 106 of the changing handle 100 cannot extend, thereby preventing axial movement of the first cam member relative to the handle. And a retaining member (e.g., a clip 110) can be coupled to the housing 20 and the first cam member 62 to retain the first cam member axially stationary therein. For example, the housing may include a circumferential channel 36 with two through-openings in communication with the internal axial bore 21 of the housing 20 such that two portions of the retainer clip 110 extend through the openings and into a retaining channel 68 of the first cam feature 62. In other embodiments, the lancing device includes other conventional structures operably coupling the first cam member in place so that is axially stationary in the housing, for example mechanical stops.

In the depicted embodiment, the handle 100 is in the form of a sleeve that coaxially receives the distal portions of the first and second cam members 62 and 80. As such, the handle 100 can be considered to form a part of the housing enclosing the internal components of the lancing device 10 (see FIGS. 1-2). In other embodiments, the handle has another conventional or new form, such as a knob or solid cylinder, so long as rotating (twisting) it drives the first cam member 62 through a rotational motion.

Furthermore, the second cam member 80 of the charging mechanism 60 is operably coupled to the lancet carrier 40 to cause the lancet carrier to axially traverse with the second cam member when the second cam member is retracted by the first cam member 62, but prevent relative rotation of the second cam member. In the depicted embodiment, for example, the second cam member 80 includes an axial bore 81 extending therethrough for receiving the tail portion 50 of the lancet carrier 40. With the tail portion 50 of the lancet carrier 40 extended through the bore 81 of the second cam member 80, the retainer projection 51 of the tail portion 50 is in its neutral state extending radially outward of the second cam bore 81 so that retracting the second cam member pulls and retracts the lancet carrier.

In addition, the end retainer attachment (e.g., a plug or clip) 92 can be placed on the tail portion 50 between the retainer projection 51 of the lancet-carrier tail portion 50 and the second cam member 80 to provide an even better connection between the two parts. Typically, the return spring 90 is also placed on the tail portion 50 before the retainer 92, so the end retainer attachment also holds it on the lancet carrier 40. In alternative embodiments, the arrangement is vice versa, with a received portion of the second cam member extending through an axial bore of the lancet carrier and a retainer of the second cam member preventing withdrawal from the lancet carrier. And in other embodiments, the second cam member and the lancet carrier include other conventional structures and arrangements operably coupling them together to provide for co-retraction, for example with the second cam member pushing the lancet carrier during retraction.

And in the depicted embodiment, for example, the second cam feature 80 includes one or more longitudinal channels 87 (see also FIG. 7) defined in the inner walls of the bore 81. With the tail portion 50 of the lancet carrier 40 extended through the bore 81 of the second cam member 80, the laterally projecting ribs 45 of the lancet carrier engage the channels 87 of the second cam member, thereby preventing rotation of the second cam member relative to the lancet carrier. In alternative embodiments, the arrangement is vice versa, with laterally projecting ribs of the second cam member engaging channels of the lancet carrier, thereby preventing relative rotation therebetween. In other embodiments, the second cam member and the lancet carrier include other conventional structures operably coupling them together to prevent relative rotation between them. And in still other embodiments, the second cam member and the lancet carrier are integrally formed as a single part.

In other embodiments, the second cam member 80 and the housing 20 include mating guidance elements that prevent relative rotation between them, independent of the mating guidance elements 26 and 44 preventing rotation between the lancet carrier 40 and the housing. Thus, in such embodiments the lancet carrier 40 may be rotational within the housing 20, and the second cam member 80 is coupled to the lancet carrier only for providing co-retraction for example by mating guidance elements such as channels and wings on the second cam member and the lancet carrier (respectively or vice versa).

Figure 7A:
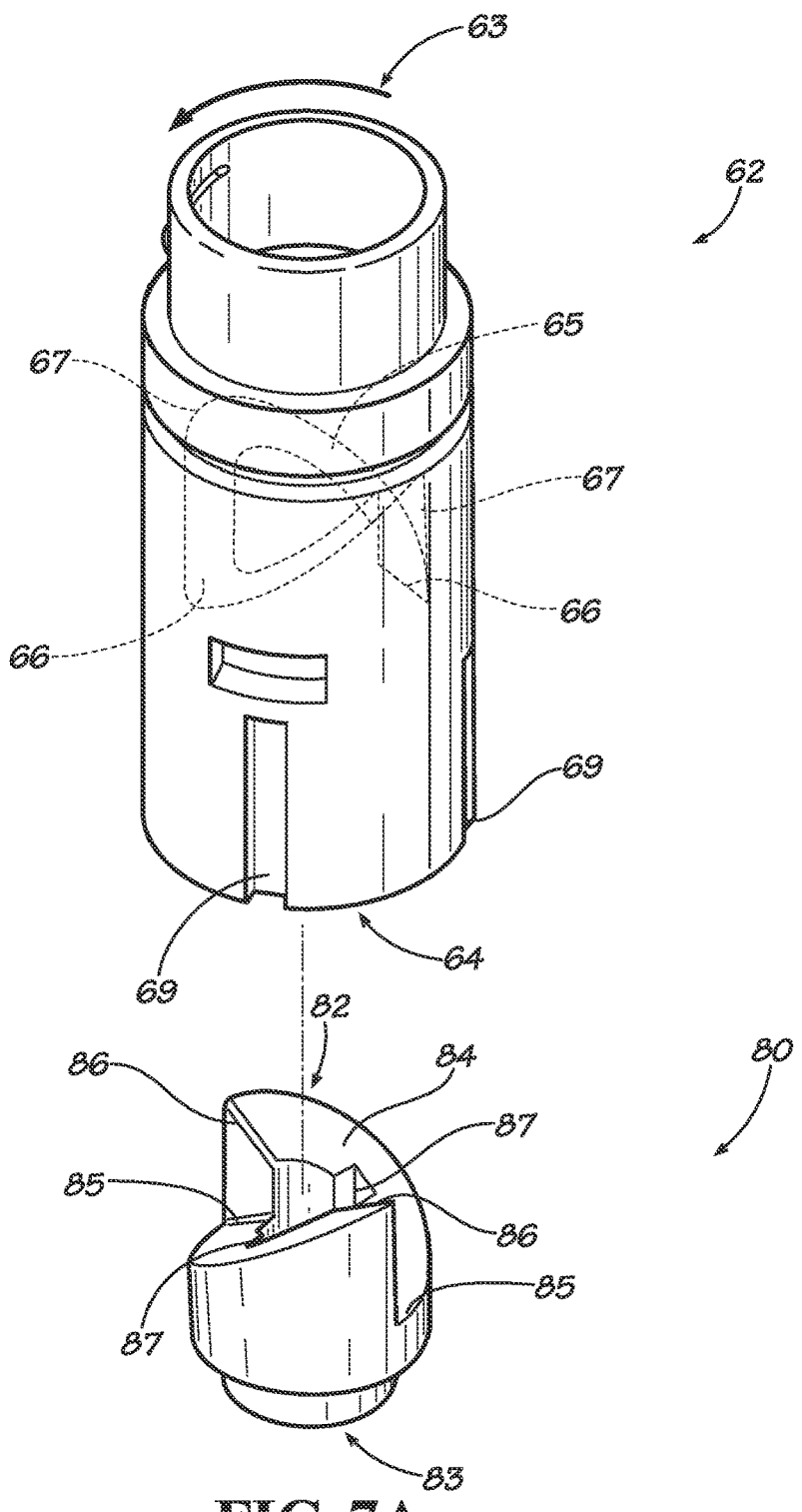
FIG. 7A is a perspective exploded view of a portion of a charging mechanism of the lancing device of FIG. 3, showing internal features thereof in phantom lines.

FIG. 7A shows the first and second cam members 62 and 80 in greater detail. In example embodiments, the cam members 62 and 80 include cam surfaces 65 and 84, respectively, that each have at least one valley portion 67 and 85 and at least one peak portion 66 and 86, respectively. As depicted, the first cam surface 65 (shown in phantom lines) is formed within an interior portion of the first cam member 62 (for example it can be defined by the axial bore 61 extending therethrough), and the second cam surface 84 is formed on the second cam member 80 (for example on its proximal end 82). In one form, the cam surfaces 65 and 84 are generally helical and/or ramp-like in shape and comprise two valley portions 67 and 85 and two peak portions 66 and 86. Preferably, the valley portions 67 and 85 of the respective cam surfaces 65 and 84 are adjacent the peak portions 85 and 86 of the cam surfaces in the uncharged/ready position, and the helical cam surfaces extending valley-to-peak therebetween are substantially similar in pitch. For example, each of the cam surfaces 65 and 84 extending between the respective valley portions 67 and 85 and peak portions 66 and 86 may span approximately 180 degrees.

As such, the second cam member 80 mounts to the distal portion of the lancet carrier 40, which extends through the first cam member 62, so that the peak portions 86 engage with the valley portions 67 of the first cam surface 65. As the first cam member 62 rotates (e.g., in a counter-clockwise direction, as indicated by the arrow) relative to the rotationally constrained second cam member 80, the peak portions 66 of the first cam surface 62 follow valley-to-peak along the second cam surface 84, thereby causing axial retracting movement of the second cam member relative to the first cam member. Thus, the angular displacement of the first cam member 62 relative to the second cam member 80 determines the axial displacement of the second cam member relative to the first cam member. In this way, rotating the handle 100 causes the first cam feature 62 to rotate, which causes the second cam feature 80 to translate, which axially displaces the carrier 40 to charge the drive spring 58 (see also FIGS. 7B-C).

In some embodiments such as that depicted, the cam surfaces 65 and 84 are ramped and generally planar. In other embodiments, the cam surfaces are ramped and include a curvature that provides greater axial movement of the second cam member and the lancet carrier at different rotational points to provide for smooth and easy operation in a reduced-size housing. In still other embodiments, the first and/or second cam surface have different shapes (while still providing the twist-to-charge functionality), such as a non-uniform pitch. And in still other embodiments, the first and/or second surfaces have an undulating shape, for example, a wave-like or sinusoidal surface having a plurality of valley portions and peak portions so that angular displacement of the first cam member (in both a clockwise or counter-clockwise direction) causes axial displacement of the second cam member.

In some embodiments, the cam members each have only one, or more than one, of the cam surfaces. In other embodiments, the helical cam surfaces are configured such that the second cam member is driven by clockwise (instead of counter-clockwise) rotation of the first cam member. In other embodiments, the first cam surface is formed on the distal end of the first cam member, instead of internally. And in other embodiments, the cam members are formed as integral parts of the lancet carrier and the handle, and thus the cam surfaces also are integral parts of the lancet carrier and the handle.

In some embodiments, the first or second cam surface is not necessarily undulating or ramped, but instead is provided by a follower surface. That is, the axial/translatory movement is all induced by one of the cam surfaces, and the other cam follower surface merely follows along the undulating or ramped cam surface. The cam follower surface can be defined on a projection (e.g., a pin or other element) of the device. In such embodiments, the projecting free end of the follower is considered its peak portion.

FIGS. 8-13 show an assembly process of the lancing device 10 (and other similar lancing devices), according to an example form of the present invention. As best seen with reference to FIG. 8, the components of the lancing device 10 are substantially assembled linearly along an axis A. Ease of assembly is provided by substantially assembling the lancing device along a single axis A within a housing 20 (e.g., a one- or two-piece housing, or any housing with an internal guidance chassis), thereby reducing the time, labor and/or equipment required to assemble.

Figure 10A:
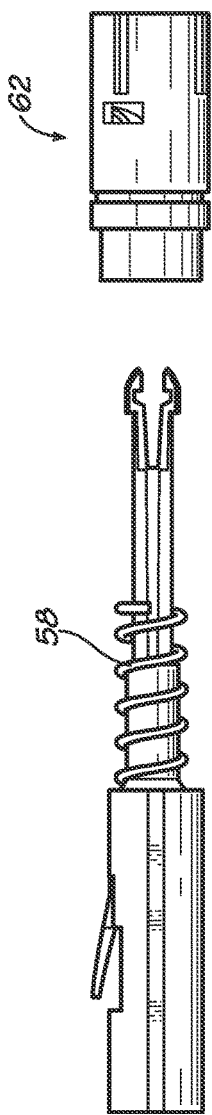
FIGS. 10a and 10b are side views of a portion of the lancing device of FIG. 8, showing a subsequent step of the assembly process.
Figure 10B:
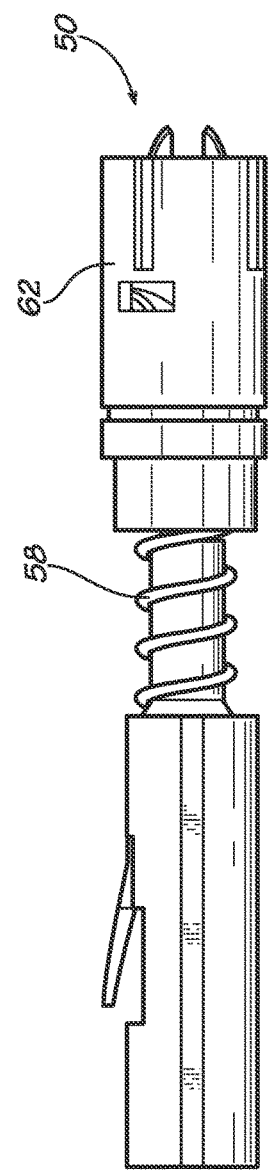
Figure 11A:
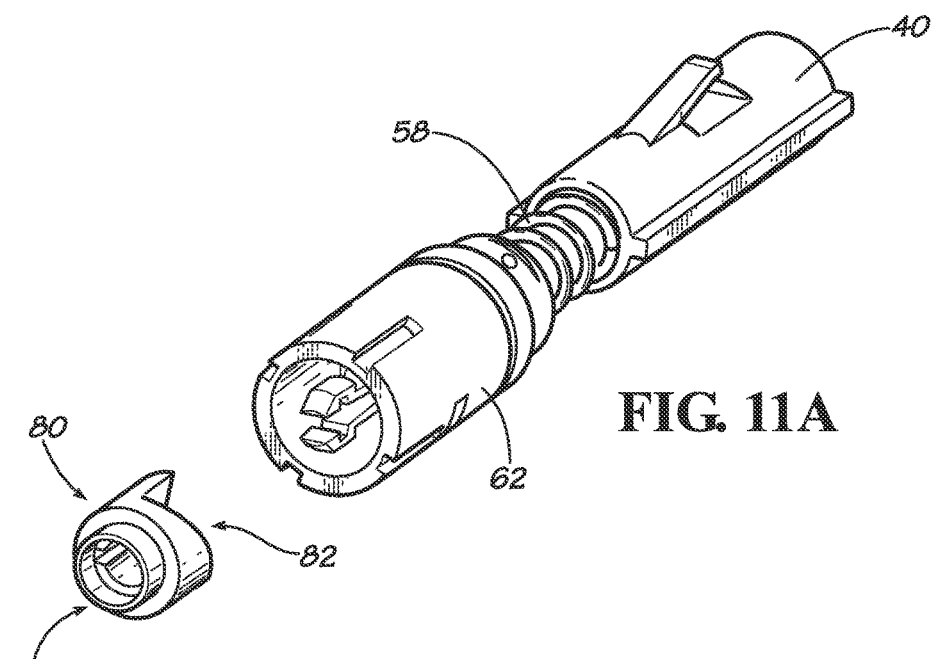
FIGS. 11A-11C are a perspective view and two side views of a portion of the lancing device of FIG. 8, showing a subsequent step of the assembly process.
Figure 11B:
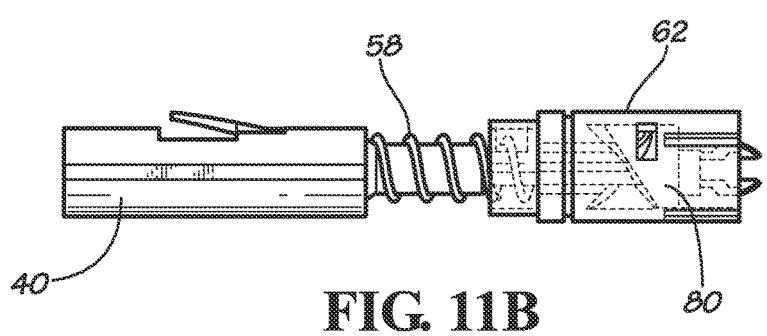
Figure 11C:
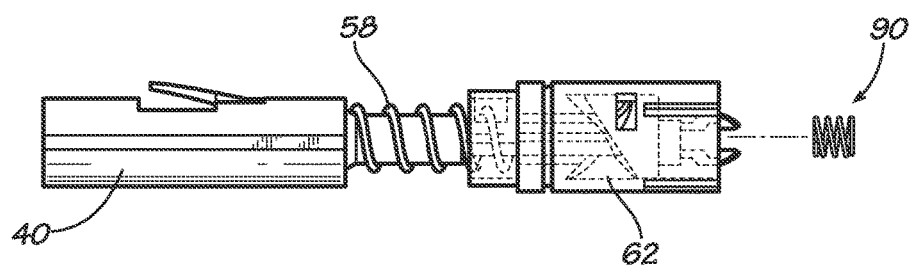
Figures 12A, 12B:
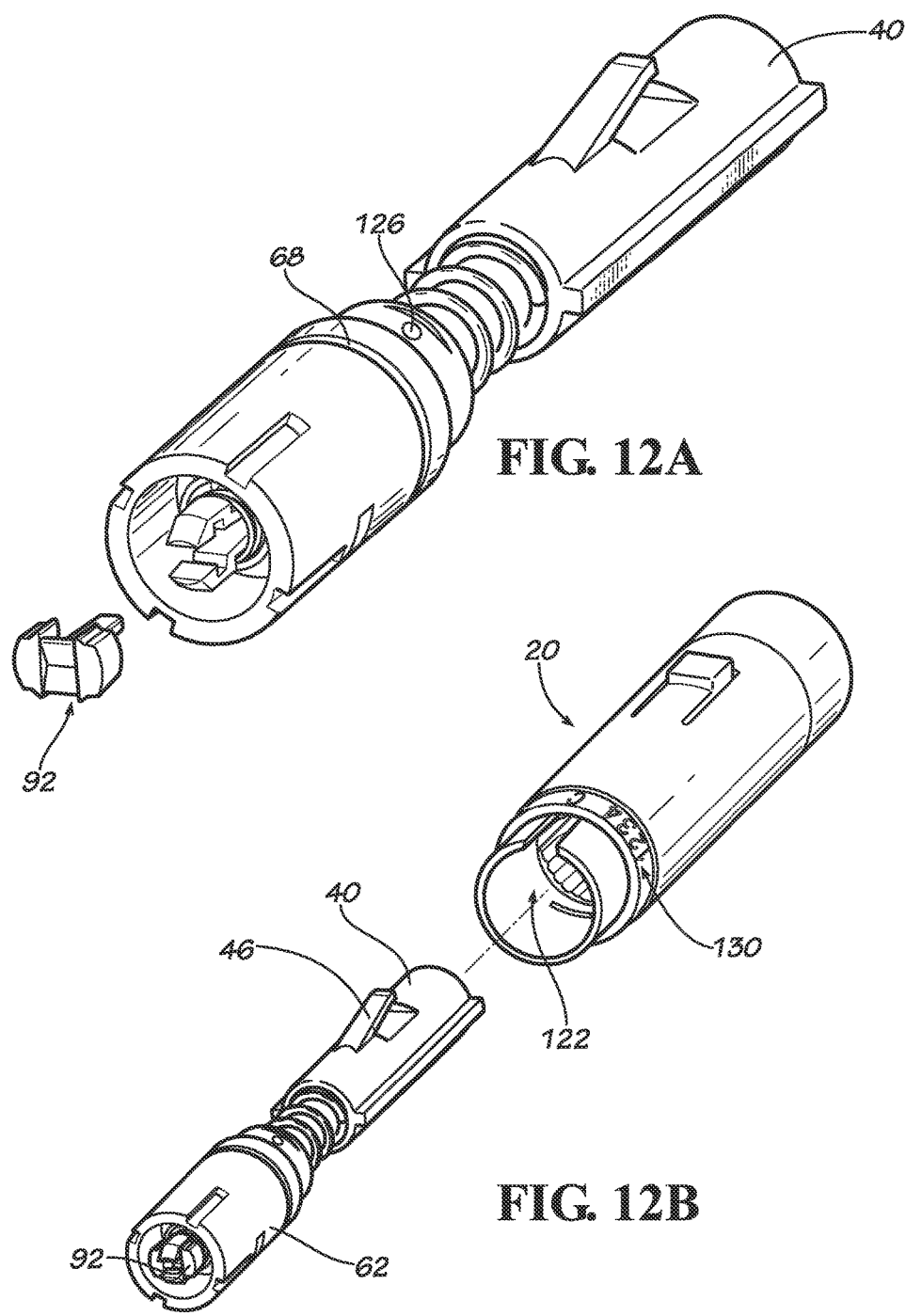
FIGS. 12a and 12b are perspective views of a portion of the lancing device of FIG. 8, showing a subsequent step of the assembly process.

FIGS. 9A-B show the installation of the drive spring 58 onto the lancet carrier 40. As depicted, the drive spring 58 is retained on the distal portion of the lancet carrier 40, wherein a portion of the drive spring 58 contacts an end surface 47 of the proximal portion of the lancet carrier 40. FIGS. 10A-B show the installation of the first cam member 62. As depicted, the tail portion 50 of the lancet carrier 40 extends through the axial bore of the first cam feature 62, and the free end of the drive spring 58 engages with a portion of the proximal end 63 of the first cam feature 62. FIGS. 11A-B show the installation of the second cam member 80 onto the lancet carrier 40. With the proximal end 82 facing towards the distal end of the lancet carrier 40, and with the ribs 45 aligned with the channels 87, the tail portion 50 of the lancet carrier 40 flexes inwardly to receive the second cam feature 80. FIGS. 11C-12A show the assembly of the return spring 90, wherein the tail portion 50 flexes inwardly to receive and retain the spring thereon. FIGS. 12A-12B show the installation of the end retainer attachment 92 onto the tail portion 50. In example embodiments, the tail portion 50 flexes outwardly to receive a central portion of the retainer attachment 92 to complete formation of a subassembly (the charging mechanism 60, drive spring 58, and lancet carrier 40).

Figure 13:
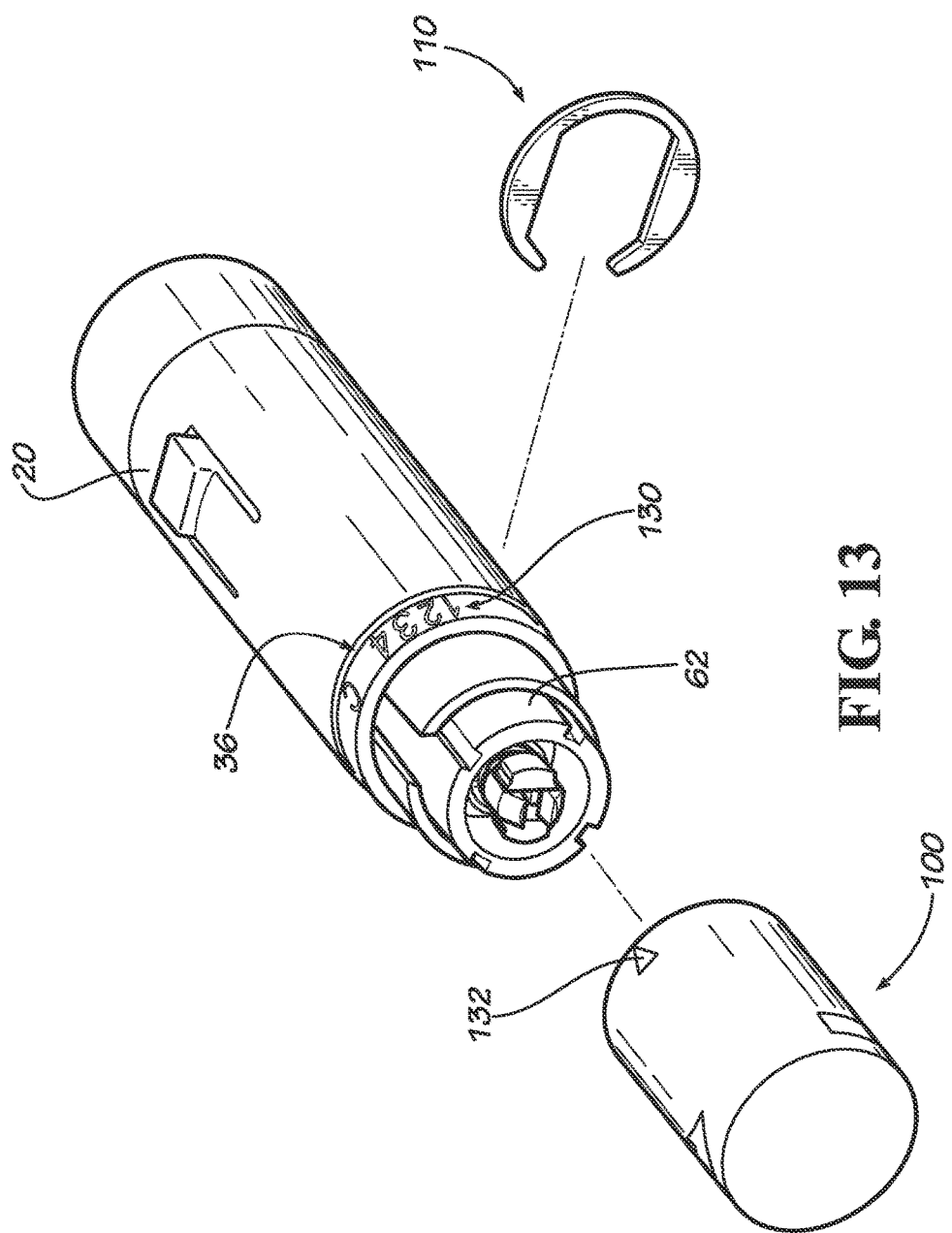
FIG. 13 is a perspective view of a portion of the lancing device of FIG. 8, showing a subsequent step of the assembly process.

After assembling the components of the subassembly, it is installed within the housing 20 (see FIGS. 12B and 13). To ensure proper installation, the lancet-carrier guide wings 44 are aligned with the housing guide slots 26, and the release finger 46 is aligned with the trigger slot 27 of the housing 20.

The subassembly is then axially positioned within the distal end of the housing 20 so that a retaining channel 68 of the first cam feature 62 (see FIG. 12A) aligns with the circumferential channel 36 of the housing 20. A retaining member or clip 110 can be coupled to the circumferential channel 36 extending around the periphery of the housing 20 and to engage a portion of the charging mechanism 60 to remain axially stationary therein. For example, the circumferential channel 36 may define at least one opening extending therethrough and within the internal axial bore 21 of the housing 20 such that at least a portion of the clip 110 extends through the opening and within the retaining channel 68 of the first cam feature 62. Thus, the subassembly is retained within the housing 20 and constrained from axial movement therein. The charging handle 100 is then coupled to the distal end 64 of the first cam feature 62 so that the inwardly projecting ribs 106 extend within and frictionally engage the slots 69 of the first cam feature 62.

Figures 7B, 7C:
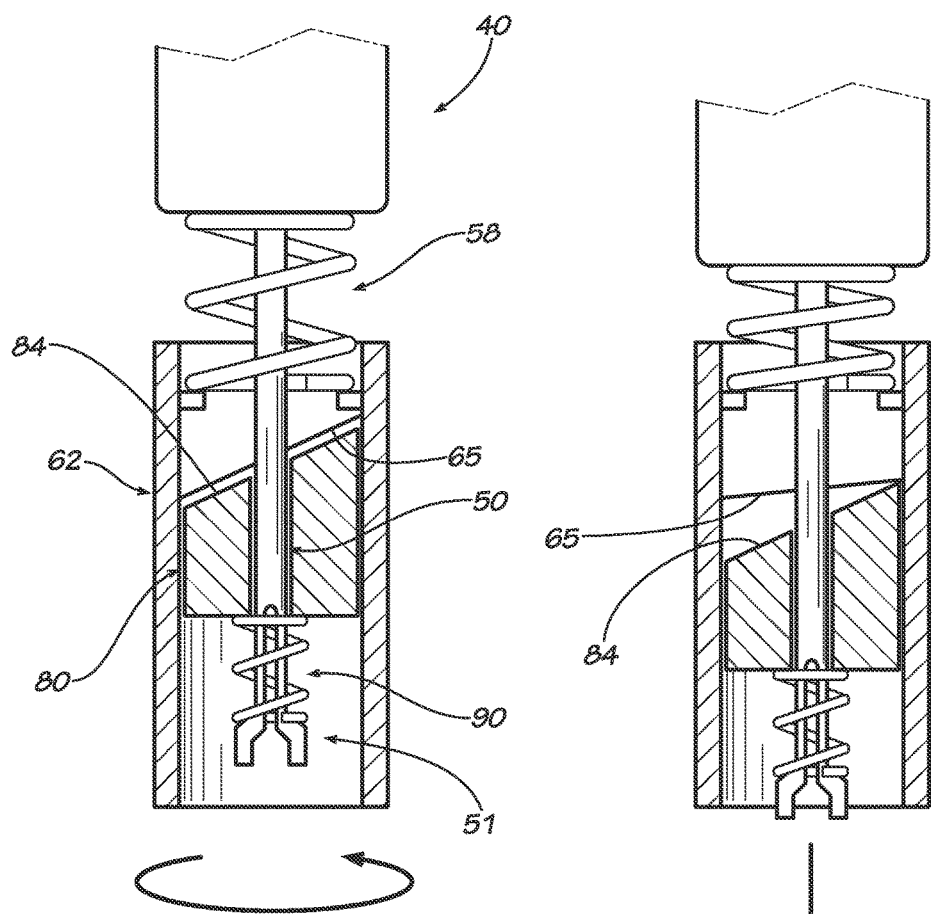
FIG. 7B is a longitudinal cross-sectional view of a portion of the charging mechanism and the lancet carrier of FIG. 3, showing the components in the uncharged state.
FIG. 7C shows the charging mechanism and the lancet carrier of FIG. 7A, with the second cam member and the lancet carrier retracted in response to rotation of the first cam member.
Figure 8:
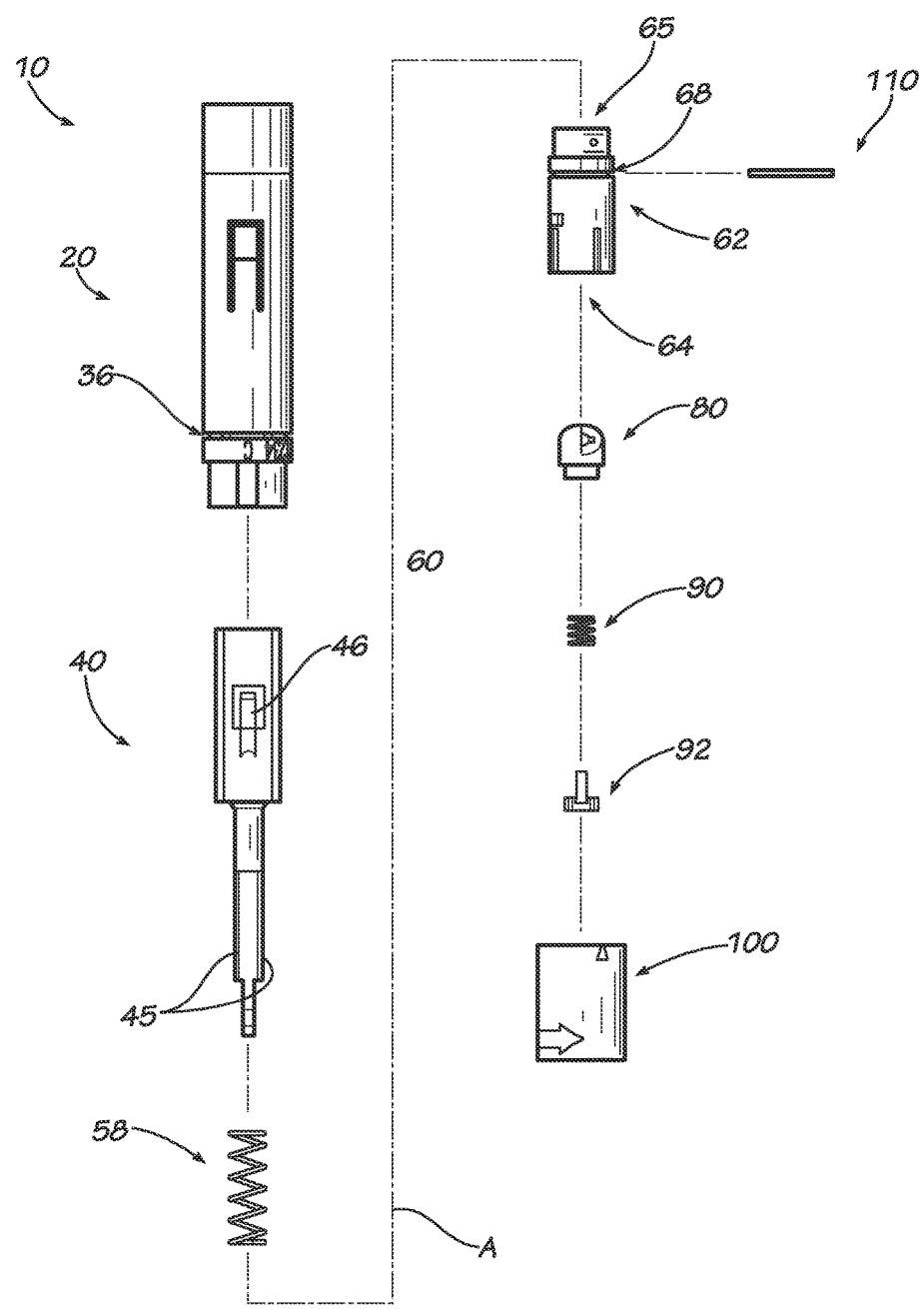
FIG. 8 is an exploded view of the lancing device of FIG. 1, showing the single-axis assembly of the lancing device according to another aspect of the invention.
Figure 14A:
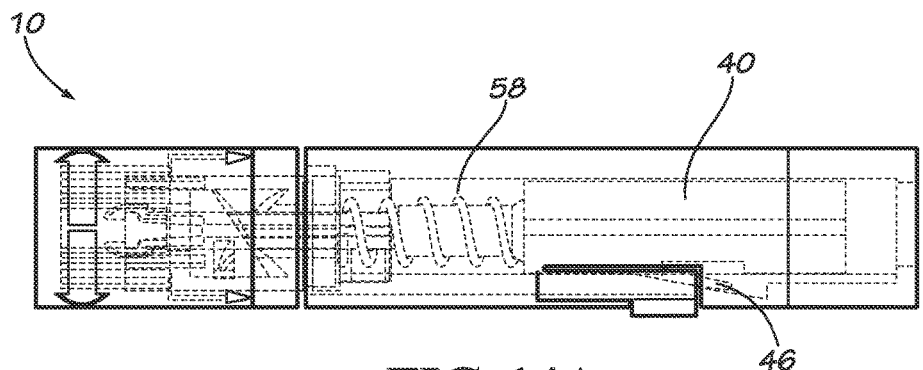
FIG. 14A-14C are cross-sectional views of the lancing device of FIG. 1 showing sequential operational movement between a neutral state, a charged state, and a fully extended state.
Figure 14B:
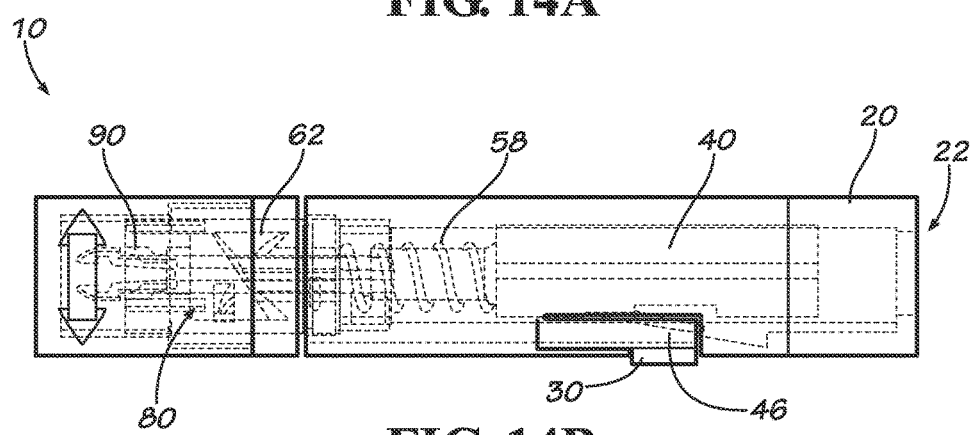
Figure 14C:
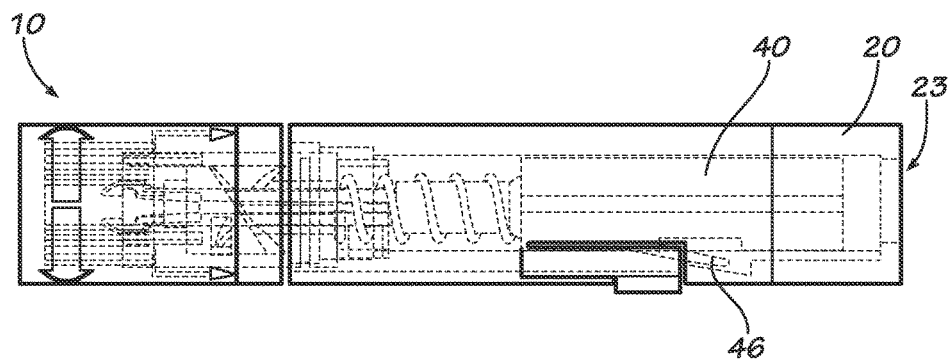

FIGS. 14A-C supplement FIGS. 7B-C to show the operation of the lancing device 10. To operate the lancing device 10, the charging handle 100 is rotated (twisted) relative to the housing 20. From a neutral state (FIG. 14A), the charging handle 100 is turned (e.g., counter-clockwise). The first cam member 62 is thereby rotated to force the peak portions 66 to follow along the cam surfaces 84 (from the valley portions 85 in the uncharged position to the peak portions 86 in the charged position) such that the second cam member 80 axially displaces rearwardly relative to the first cam feature 62. Upon the peak portions 66 of the first cam surface 65 moving beyond the peak portions 86 of the second cam surface 84, the release finger 46 of the lancet carrier 40 constrained to traverse within the trigger slot 27 releasably engages with the contact face 34 of the housing 20, thereby charging the lancet carrier 40 (FIG. 14B). With the lancing device charged, actuation of the release button 30 removes the release finger 46 from the contact face 34 to initiate the lancing stroke, thereby resulting in the lancet carrier 40 moving from a retracted position within the housing 20 to an advanced or fully extended position wherein at least the sharp tip portion of the lancet projects externally of the lancet opening 23 to penetrate the subject's skin at a lancing site (FIG. 14C).

In further example embodiments, the lancing device 10 may include a depth-adjustment mechanism integrally formed therein. As shown in FIGS. 12A-B, the housing 20 can comprise internally projecting ribs or detents 122 and a plurality of grooves defined therebetween arranged along a portion of the internal surface thereof, and the first cam member 62 can comprise an outwardly projecting detent 126 for removably engaging therewith. For example, the outwardly projecting detent 126 can engage a plurality of internally projecting ribs 122 that each correspond to a particular angular position. In example embodiments, the charging handle 100 is turned until the lancet carrier retracts to provide the release finger 46 engagement with the contact surface 34. Further rotation of the charging handle 100 determines the angular positions of the peak portions 66 relative to the angularly constrained cam surfaces 84 of the second cam feature 80, thereby constraining the axial displacement of the lancet carrier 40 (and the second cam member 80 mounted thereto) relative to the housing 20. Optionally, depth-indication indicia (e.g., numerals) 130 can be placed along the periphery of the housing 20 such that a depth-indication marking 132 of the charging handle 100 (see FIG. 13) corresponds to the depth of penetration.

In further example embodiments, the housing 20 can include a cam surface for engaging a cam surface of a charging handle such that rotation of the charging handle relative to the housing retracts the lancet carrier to a charged state. When the charging handle is so rotated, it is axially displaced by at least one biasing spring that couples the housing and the handle together.

While the invention has been described with reference to preferred and example embodiments, it will be understood by those skilled in the art that a variety of modifications, additions and deletions are within the scope of the invention, as defined by the following claims.

What is claimed is:

1. A lancing device for propelling a lancet through a lancing stroke, the lancing device comprising:
   a housing including an axial bore;
   a lancet carrier translational within the housing through the lancing stroke, the lancet coupleable to the lancet carrier;
   a drive spring for propelling the lancet carrier forward through the lancing stroke, wherein the drive spring comprises a first end and a second end; and
   a charging mechanism including a first cam member, a second cam member, and a rotatable handle, wherein the first cam member is mounted within the housing, rotatable relative to the housing, and restricted from axial translation relative to the housing, the second cam member abuts the first cam member, is coupled to the lancet carrier to provide co-translation, and is restricted from rotation relative to the housing, and the rotatable handle is co-rotationally attached to the first cam member,
   wherein rotation of the handle rotates the first cam member therewith, causing the first cam member to rotate against the second cam member, which in response translates the second cam member axially because it is restricted from rotation, thereby retracting the coupled-thereto lancet carrier to a charged position; and
   wherein the first end of the drive spring directly engages the lancet carrier and the second end of the drive spring directly engages the first cam member.

2. The lancing device of claim 1, wherein the first cam member, the second cam member, or both, include at least one cam surface having the form of a helical ramp.

3. The lancing device of claim 2, wherein the at least one helical-ramp cam surface extends about 180 degrees about an axis of the respective cam member.

4. The lancing device of claim 1, wherein the first cam member includes a first cam surface having a peak portion and a valley portion, the second cam member includes a second cam surface having a peak portion and a valley portion, and wherein rotation of the handle causes the first cam surface to move along the second cam surface to the charged position in which the peak portion of the first cam surface contacts the peak portion of the second cam surface.

5. The lancing device of claim 4, wherein the first cam member rotates to the charged position from an uncharged position in which the peak portion of the first cam surface contacts the valley portion of the second cam surface.

6. The lancing device of claim 1, wherein the rotatable handle is co-rotationally attached to the first cam member by one or more ribs on one of the handle and the first cam member and one or more slots on the other one of the handle and the first cam member that mate with the ribs.

7. The lancing device of claim 1, wherein the lancet carrier is coupled to the second cam member so that they translate together by a resiliently deflectable tail portion of the lancet carrier extending through an axial bore of the second cam member.

8. The lancing device of claim 1, wherein the second cam member is restricted from rotation relative to the housing by one of a rib and channel on the second cam member mating with the other one of the rib and channel on another element of the lancing device.

9. The lancing device of claim 1, wherein the second cam member is restricted from rotation relative to the housing by being restricted from rotation relative to the lancet carrier and the lancet carrier being restricted from rotation relative to the housing.

10. The lancing device of claim 1, wherein the lancet carrier is restricted from rotation relative to the housing and guided along translation relative to the housing by one or more wings on one of the lancet carrier and the housing and one or more slots on the other one of the lancet carrier and the housing that mate with the wings.

11. The lancing device of claim 1, wherein the first cam member includes an axial bore and the lancet carrier includes a tail portion that extends through the axial bore of the first cam member and couples to the second cam member so that the first cam member is positioned between the second cam member and a lancing opening of the housing through which the lancet at least partially extends during the lancing stroke.

12. The lancing device of claim 1, wherein the handle and the first cam member are separate components that are assembled together, and the lancet carrier and the second cam member are separate components that are assembled together.

13. The lancing device of claim 1, wherein the housing includes a plurality of internally projecting ribs and a plurality of grooves defined therebetween, and the first cam member includes a detent that selectively engages the grooves to provide depth adjustment of the lancing stroke.

14. A charging mechanism for a lancing device for propelling a lancet through a lancing stroke, the lancing device comprising a housing including an axial bore, a lancet carrier translational within the housing through the lancing stroke with the lancet coupled to the lancet carrier, and a drive spring for propelling the lancet carrier through the lancing stroke, the charging mechanism comprising:
 a first cam member mounted within the housing, rotatable relative to the housing, restricted from axial translation relative to the housing, defining a first cam surface having a peak portion and a helical ramp extending about 180 degrees about an axis of the first cam member, and having an axial bore extending therethrough;
 a second cam member abutting the first cam member, coupled to the lancet carrier to provide co-translation, restricted from rotation relative to the housing, and defining a second cam surface having a peak portion; and
 a rotatable handle co-rotationally attached to the first cam member,
 wherein rotation of the handle rotates the first cam member therewith, causing the peak portion of the first cam surface to rotate against the second cam surface until it engages the peak portion of the second cam surface, which in response axially translates the second cam member because it is restricted from rotation, thereby retracting the coupled-thereto lancet carrier to a charged position; and
 wherein the second cam member is contained entirely within the axial bore of the first cam member.

15. The lancing device of claim 14, wherein the second cam surface has a helical ramp extending about 180 degrees about an axis of the second cam member, wherein the helical ramp of the first cam member is configured to align with the helical ramp of the second cam member in an uncharged position.

16. The lancing device of claim 14, wherein one of the first cam surface and the second cam surface includes a valley portion against which the peak portion of the other one of the first cam surface and the second cam surface contacts when the charging mechanism is in an uncharged position.

17. The lancing device of claim 14, wherein second cam member is restricted from rotation relative to the housing by being restricted from rotation relative to the lancet carrier and the lancet carrier being restricted from rotation relative to the housing.

18. The lancing device of claim 14, wherein the lancet carrier includes a tail portion that extends through the axial bore of the first cam member and couples to the second cam member so that the first cam member is positioned between the second cam member and a lancing opening of the housing through which the lancet at least partially extends during the lancing stroke.

19. The lancing device of claim 18, wherein the second cam member includes an axial bore and wherein the tail portion of the lancet carrier extends through the axial bore of the second cam member.

20. The lancing device of claim 14, wherein the handle and the first cam member are separate components that are assembled together, and the lancet carrier and the second cam member are separate components that are assembled together.

* * * * *